US011986256B2

(12) United States Patent
Nahum et al.

(10) Patent No.: US 11,986,256 B2
(45) Date of Patent: *May 21, 2024

(54) AUTOMATIC REGISTRATION METHOD AND DEVICE FOR SURGICAL ROBOT

(71) Applicant: MedTech S.A., Montpellier (FR)

(72) Inventors: Bertin Nahum, Baillargues (FR); Lucien Blondel, Montpellier (FR); Pierre Maillet, Saint Aunes (FR)

(73) Assignee: MedTech S.A., Montpellier (FR)

( * ) Notice: Subject to any disclaimer, the term of this patent is extended or adjusted under 35 U.S.C. 154(b) by 128 days.

This patent is subject to a terminal disclaimer.

(21) Appl. No.: 17/690,781

(22) Filed: Mar. 9, 2022

(65) Prior Publication Data

US 2022/0192757 A1 Jun. 23, 2022

Related U.S. Application Data

(63) Continuation of application No. 16/087,011, filed as application No. PCT/FR2017/050662 on Mar. 21, 2017, now Pat. No. 11,298,193.

(30) Foreign Application Priority Data

Mar. 21, 2016 (FR) ...................................... 1652414

(51) Int. Cl.
A61B 34/20 (2016.01)
A61B 34/30 (2016.01)
(Continued)

(52) U.S. Cl.
CPC ............. *A61B 34/20* (2016.02); *G16H 40/60* (2018.01); *A61B 2017/00057* (2013.01);
(Continued)

(58) Field of Classification Search
CPC . A61B 34/20; A61B 34/30; A61B 2034/2055; A61B 2034/2057;
(Continued)

(56) References Cited

U.S. PATENT DOCUMENTS 6,298,262 B1  10/2001  Franck et al.
7,072,707 B2   7/2006  Galloway, Jr. et al.
(Continued)

FOREIGN PATENT DOCUMENTS

EP   1857070 A1   11/2007
EP   2467080 B1    4/2018
(Continued)

OTHER PUBLICATIONS

U.S. Appl. No. 16/087,011, filed Sep. 20, 2018, Automatic Registration Method and Device for Surgical Robot.
(Continued)

Primary Examiner — Boniface N Nganga
(74) Attorney, Agent, or Firm — SCHWEGMAN LUNDBERG & WOESSNER, P.A.

(57) ABSTRACT

This invention concerns an automated registration method and device for a surgical robot enabling registration between a first three-dimensional location system comprising an optical distance sensor and a second three-dimensional location system comprising optical acquisition means. The method comprises:
  a first step of intraoperative registration between the first location system and data recorded on an anatomical surface of a patient and;
  a second step of intraoperative registration of two three-dimensional location systems.
The second registration step is performed at the same time as the first registration step by detection, by the optical
(Continued)

Figure 1:
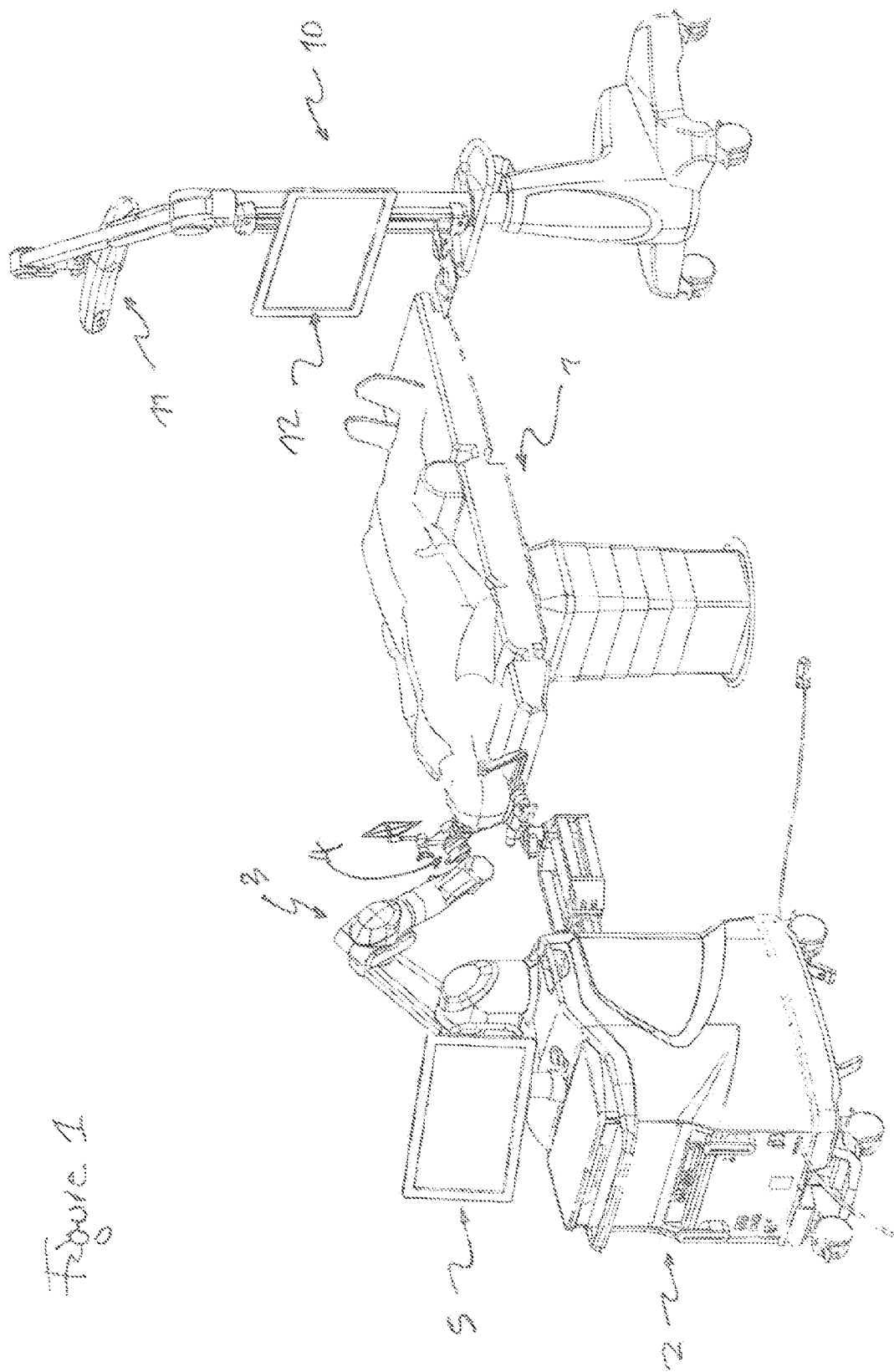

acquisition means, of at least one point of a point cloud acquired by the optical sensor during the first intraoperative registration.

20 Claims, 2 Drawing Sheets

(51) Int. Cl.
  *A61B 90/00*   (2016.01)
  *G16H 40/60*   (2018.01)
  *A61B 17/00*    (2006.01)
(52) U.S. Cl.
  CPC .............. *A61B 2034/2055* (2016.02); *A61B 2034/2057* (2016.02); *A61B 34/30* (2016.02); *A61B 2090/061* (2016.02); *A61B 2090/364* (2016.02)
(58) Field of Classification Search
  CPC .... A61B 2017/00057; A61B 2090/061; A61B 2090/364; G16H 40/60
  See application file for complete search history.

(56) References Cited

U.S. PATENT DOCUMENTS

| 11,298,193 | B2* | 4/2022 | Nahum ............... G16H 40/60 |
| 2005/0148859 | A1 | 7/2005 | Miga et al. |
| 2006/0072124 | A1 | 4/2006 | Smetak et al. |
| 2008/0118143 | A1 | 5/2008 | Gordon et al. |
| 2008/0123927 | A1 | 5/2008 | Miga et al. |
| 2010/0172567 | A1 | 7/2010 | Prokoski |
| 2010/0228117 | A1 | 9/2010 | Hartmann |
| 2012/0109150 | A1 | 5/2012 | Quaid et al. |
| 2014/0003705 | A1 | 1/2014 | Taguchi et al. |
| 2015/0150645 | A1 | 6/2015 | Woerlein et al. |
| 2016/0030131 | A1 | 2/2016 | Yang et al. |
| 2017/0238998 | A1 | 8/2017 | Srimohanarajah et al. |
| 2019/0099222 | A1 | 4/2019 | Nahum et al. |

FOREIGN PATENT DOCUMENTS

| FR |     3048872 A1 | 9/2017 |
| WO | WO-2005025404 A2 | 3/2005 |
| WO | WO-2012017167 A1 | 2/2012 |
| WO | WO-2016066287 A1 | 5/2016 |
| WO | WO-2016205915 A1 | 12/2016 |
| WO | WO-2017162981 A1 | 9/2017 |

OTHER PUBLICATIONS

"U.S. Appl. No. 16/087,011, Advisory Action dated Oct. 28, 2021", 3 pgs.
"U.S. Appl. No. 16/087,011, Final Office Action dated Aug. 9, 2021", 18 pgs.
"U.S. Appl. No. 16/087,011, Non Final Office Action dated Nov. 24, 2020", 16 pgs.
"U.S. Appl. No. 16/087,011, Notice of Allowance dated Dec. 8, 2021", 9 pgs.
"U.S. Appl. No. 16/087,011, Notice of Non-Compliant Amendment dated Mar. 8, 2021" 3 pgs.
"U.S. Appl. No. 16/087,011, Response filed Feb. 24, 2021 to Non Final Office Action dated Nov. 24, 2020", 10 pgs.
"U.S. Appl. No. 16/087,011, Response filed May 10, 2021 to Notice of Non-Compliant Amendment dated Mar. 8, 2021", 6 pgs.
"U.S. Appl. No. 16/087,011, Response filed Oct. 8, 2021 to Final Office Action dated Aug. 9, 2021", 10 pgs.
"International Application Serial No. PCT/FR2017/050662, International Search Report dated Jun. 19, 2017", (W/ English Translation), 7 pgs.
"International Application Serial No. PCT/FR2017/050662, Written Opinion dated Sep. 28, 2017", (W/ English Translation), 11 pgs.

* cited by examiner

AUTOMATIC REGISTRATION METHOD AND DEVICE FOR SURGICAL ROBOT

This invention applies to the medical field and, more particularly, to the field of robotic-assisted surgery, typically used when high operating precision is required.

It concerns what is conventionally called registration, i.e. matching the registration frames of reference in space of the different elements, equipment, and tools that are involved in the operation (including the patient, or more specifically the region or regions of intervention on the patient). Yet more precisely, the invention relates to a method of automated registration between two three-dimensional location systems and a surgical robotic-assisted device implementing said method.

This registration is performed during the intraoperative phase, in practice at the start of the operation, just before the surgical procedure begins. Said registration is vitally important in ensuring an acceptable degree of precision of the automated operating procedures, since it results in all of the instruments used as well as the intervention area, unless directly calibrated on the same frame of reference, being in any event connected by transfer matrices from one frame of reference to the other. In this particular case, the transfer matrices, calculated during the registration phase, enable each system of coordinates relating to a frame of reference to be transformed and therefore be intelligible in another frame of reference.

The idea behind the registration procedure is to unify the working reference of all of the parts involved in the robotic-assisted surgical operation, which means that each device can exploit in real time positioning measurements, if necessary taken in a frame of reference that is not its own, for example connected to other instruments used during the surgical operation. The problem arises from the fact that several separate frames of reference coexist. An example of these reference points includes the reference point of measurements deriving from a medical examination, the reference point of a surgical-assistance robot, the reference point of an optical navigator and the reference point of the anatomical region to be treated on the body of the patient lying on the operating table. They are all to be taken into consideration in order to work in an approved manner.

Registration requires measurements and, in this field, is based mainly on optical imaging techniques since it chiefly involves locating anatomical surfaces of the patient around the operation area. Before any other processing takes place, they must be matched up with the imaging data resulting from medical examinations performed by conventional means (radiological examinations with CT scans, Magnetic Resonance Imaging (MRI), etc.) so that the surgeon's forecast operation objectives can be implemented in the reality of the operating theatre, integrating the different instruments required and their locations and respective reference points. This is a first registration that is then implemented: more precisely, in the configurations of surgical operations using assistance robots which will be described later by way of example, the assistance robot equipped with surgical tools or instruments to assist the surgeon must therefore undergo such a registration procedure. This involves the acquisition of a point cloud of the anatomical surface, or at least a few points of a surface of a patient, on the basis of which it is possible to draw a comparison between, on the one hand, the reference point of the robot on which the instruments depend and, on the other, the frame of reference used for the description of the part of the patient's body concerned.

In practice, it is a surface scan that is performed during said first registration procedure, enabling the acquisition of the targeted anatomical surface. The system then creates a three-dimensional representation in the form of a digital model, formed from a point cloud, which if necessary is processed (selection of significant points) with a view to drawing a comparison with the data resulting from radiological or MRI (magnetic resonance imaging) examinations on the same patient that have be pre-recorded and from which it is possible to obtain surface parameters suitable for the comparison and therefore the desired registration.

A surgical-assistance robot locates the instruments that it carries using the information from encoders of each of its axes, in a reference point usually defined at its base and aligned along the first axis. It in fact behaves as a three-dimensional location system. Since the surgical actions in which it is used (brain surgery, operations on the vertebral column) require extreme precision in positioning the instruments and in surgical procedures, it must if necessary be capable of adapting to the movements of the anatomical surfaces on which it is used. These may, for example, be movements of the vertebral column resulting from the patient's respiration, or possible head movements during a neurosurgical operation. It needs to adapt, in real time, the position of the tools in relation to the proposed operation targets and so constantly receive information on any movements of said targets.

An optical navigator, which is another three-dimensional location system, is to this end more and more often associated with surgical-assistance robots in current operation protocols, a navigator that operates according to its own reference point and must of course also be based on the reference points relating to the patient on the one hand and the surgical robot on the other.

On this assumption there is an optical navigator as well as the surgical-assistance robot, once the patient is positioned on an operating table and immobilized in relation thereto, he is placed as stated so as to match up with the reference point that relates to him and that relates to the surgical-assistance robot during a first registration. At this stage, the optical navigator has not yet received any information regarding the position of the robot and that of the anatomical surfaces involved in the operation in progress. A second registration operation must therefore be performed in order to connect the three reference points that exist in this case.

The problem, an old one, is less of an issue now that efforts are made to subjugate surgical robots to navigators capable of detecting body movements likely to distort the position of the surgical instruments and tools. In this regard, at least two types of methods are known that allow the anatomical surfaces to be identified in the robot's frame of reference, and to harmonize or in any case allow the inter-location of the robot's frames of reference, the anatomical surfaces of the patient being operated on and the optical navigator.

A first type of known method of relative location between a surgical-assistance robot and an optical navigator, described in document US 2012/109150, involves on the one hand a robotic arm equipped with an optical target (for example reflective spheres) and having six degrees of freedom, and on the other an optical navigator equipped with optical detection means. After a first registration involving the robot and anatomical surfaces, a second registration has the objective of strictly matching the frames of reference of the robot and navigator. The robotic arm carries for this purpose at least one target of known geometry, placed on the tool or the instrument equipping the arm, and which carries for example reflective spheres. The optical navigator can then precisely locate the instruments equipped with an optical target thanks to the information on the position of the reflective spheres, obtained by triangulation from information detected by an optical acquisition system equipping the navigator.

The operating method for registration is as follows: the robotic arm is moved so as to assume a certain number of predetermined fixed positions (six, for example) framing the working space. An acquisition of the coordinates of each position is taken both in the frame of reference of the robotic arm, by recording the positions of the tool in the reference point of the robot, and in the frame of reference of the optical navigator, after triangulation. This acquisition generates a cloud of coordinates in each frame of reference, and computer processing allows the frames of reference of the robot and optical navigator to be strictly matched by calculating a transfer matrix of the coordinates of the point cloud of one frame of reference to the other.

This type of method of relative location has the drawback of requiring two different steps of acquisition, on the one hand to locate the anatomical surfaces of the patient in the reference point of the robot and on the other to calculate the correspondence between the reference point of the robotic arm and the reference point of the navigator, which results in an increase in operation time. It then requires the robot to be placed in a succession of specific positions in relation to the optical navigator, and consequently involves some movements creating a risk of collision due to the customary clutter in operating theatres. Lastly, it requires additional equipment, namely the reflective-sphere target or targets.

Another registration method category, described in document U.S. Pat. No. 6,298,262, performs an acquisition of the anatomical surfaces of the patient with the aid of an optical pointer (laser) equipped with at least one optical target, manipulated by an operator in order to target a succession of points of the anatomical surface affected by or near the surgical operation. The operator scans this anatomical surface with the laser transmitter (and within it identifies approximately 200 points). During this scanning, an optical navigator performs an acquisition of the positions identified so as to build a point cloud in its own frame of reference. A registration step is then performed to match the frame of reference of the optical navigator to that of the patient, on the basis of medical images acquired beforehand by conventional imaging techniques (scans or MRI).

This second type of method, which is not based on a robot/navigator registration, has the drawback of lacking precision and not having a high degree of reproducibility. The acquisition of the anatomical surfaces depends in fact on a human operator and his expertise. Moreover, it requires an additional device, the optical pointer used by the operator for his manual scan.

This invention overcomes the above-mentioned drawbacks and problems and proposes a method of registration between two three-dimensional location systems that is simpler than its precursors. This simplification affects the method itself, by the elimination of steps, but it also has its origin in the corresponding elimination of the additional equipment used in the methods of the prior art. The reliability of the method obtained is considerably improved.

The registration method of the invention, usually implemented between two three-dimensional location systems used in robotic surgery in order to match up location data from separate frames of reference belonging to each system, is applied to a first three-dimensional location system comprising an optical distance sensor and a second three-dimensional location system comprising optical acquisition means.

It is implemented by performing a first intraoperative registration step between the first location system and data recorded on an anatomical surface of a patient, obtained from the surface using a technique described in document WO 2012/017167, involving the matching of at least one point of a cloud point acquired during an intraoperative phase on said surface by means of an optical distance sensor and one point of a collection of points of said data, and it comprises a second step of intraoperative registration of both three-dimensional location systems.

Lastly, the said second step of registration is performed at the same time as the first step of registration by detection, by the optical acquisition means, of at least one point of the cloud point acquired by the optical sensor during the first intraoperative registration.

The innovation lies chiefly in the fact that the method allows the specific registration phase between the robot and the optical navigator to be skipped, like examples of three-dimensional location systems, by directly using the available data deriving from the registration performed between the robot and the patient on the basis of a surface method. In other words, the two registrations are combined by using the same starting data, which results in reducing the operating time and eliminating the manipulation and movement of equipment due to the existence of targets. The benefits of the innovation are therefore multiple, both in terms of methodology and as regards the equipment required.

Preferably, according to the invention, the second registration step involves calculating a transfer matrix between the two frames of reference of the two three-dimensional location systems.

Moreover, according to one possibility, the optical distance sensor of the first three-dimensional location system can be a laser telemeter projecting a laser beam onto the anatomical surface of the patient. The optical acquisition means of the second three-dimensional location system may consist in at least one camera for the acquisition of optical signals in the form of light points projected onto a surface.

The method can in practice be applied to all systems equipped with a three-dimensional location device comprising a laser, and a three-dimensional system based on detection cameras. In this regard, the optical distance sensor and at least one means of acquisition of optical signals are tuned on the same wavelengths.

Preferably, according to the invention, the wavelengths used can be in the infrared range, although clearly this choice can be altered depending on the technical characteristics required. More particularly, according to a preferential application that has so far been taken as an example but is in no way limiting as regards the invention, the first three-dimensional system can be a surgical-assistance robot and the second three-dimensional location system can be an optical navigator. The invention also concerns a surgical-assistance robotic medical device such that the first three-dimensional location system can be a surgical-assistance robot and the second three-dimensional location system can be an optical navigator.

More precisely, it emerges from the previous description that the surgical-assistance robot can then be equipped with a robotic arm the free end of which is equipped with a laser-telemeter optical distance sensor. Preferably, the surgical-assistance robot (2) has six degrees of freedom.

Similarly, the optical navigator can be equipped with optical signal acquisition means of the infrared camera type.

Figure 2:
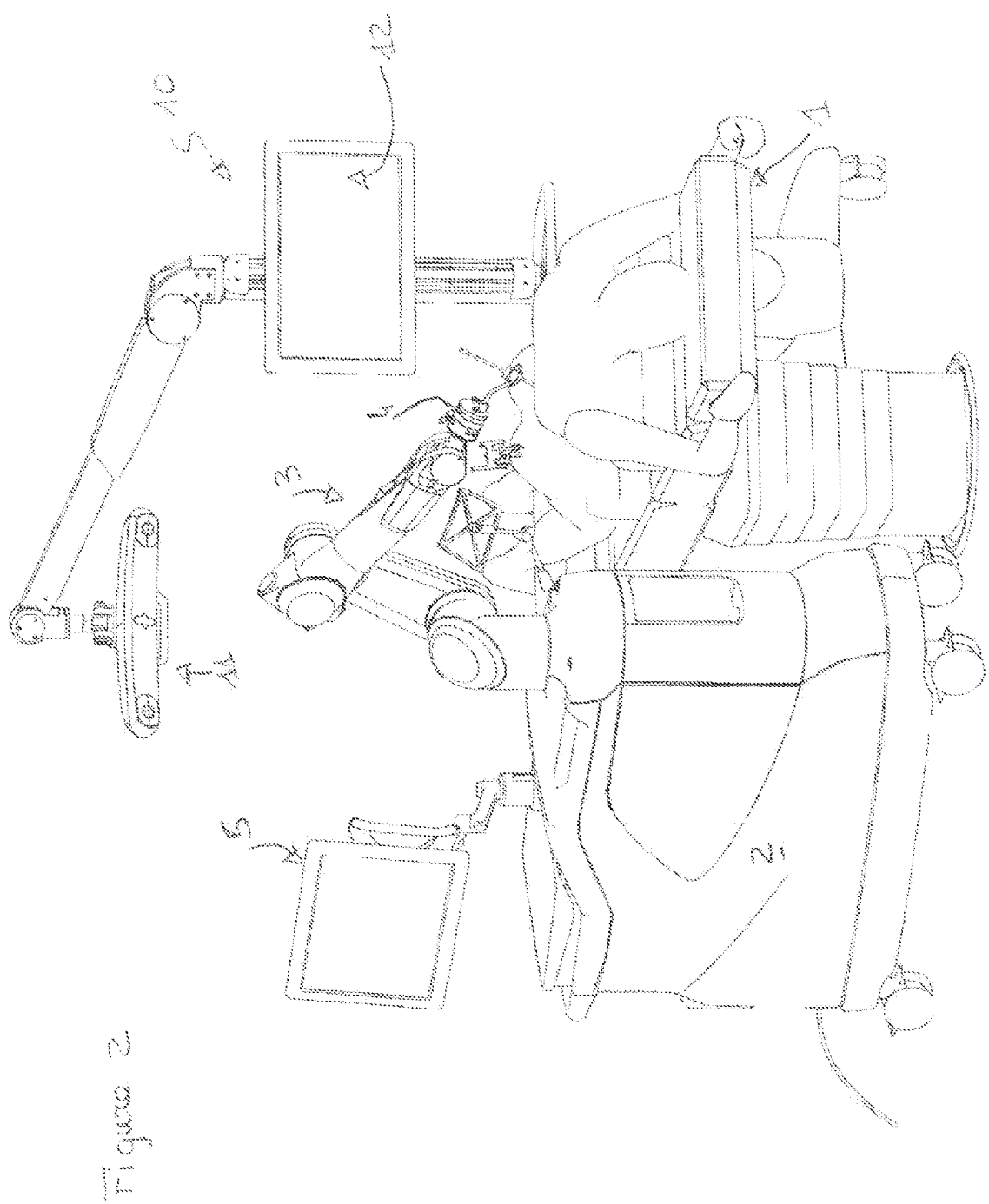

Other features and advantages of the invention will emerge from the following detailed description of two embodiments, shown in the accompanying figures, in which:

FIG. 1 is a perspective view of the complete operation device used for an operation on the head, for example the brain; and FIG. 2 represents a perspective view of an equivalent operation device but for a surgical operation performed on the vertebral column.

With reference to FIGS. 1 and 2, the patient lies on his back (FIG. 1) or stomach (FIG. 2) on an operating table (1), near a surgical-assistance robot (2) that comprises a movable box on wheels surmounted by a robotic arm (3) the free end of which can be equipped with at least one surgical tool or at least one optical distance sensor (4). The robot shown in FIG. 1 is provided for neurosurgical operations, whereas the one shown in FIG. 2 instead concerns surgery on the vertebral column. Moreover, it has an assistance screen (5) allowing the operator, in this case the surgeon, to view the operation in progress and more precisely the work of the tool fitted on the robotic arm (3). The end of the robotic arm (3) also comprises a laser telemeter operating for example in the infrared range. It is moved by the robot (2) over the patients face (in the example shown in FIG. 1) and more generally over the anatomical area that is to be scanned by the optical distance sensor, identifies a succession of points forming a cloud point that the system continuously records on the surface of the skin in order to perform the first registration between the reference point relating to the patient (deriving from recorded images) and the reference point reported to the robot (2). For an operation on the brain, these points are located on the patient's temples, nose and forehead. In the case of an operation on the vertebral column, the recorded points are located near the area to be operated upon.

This point cloud, in practice constituting a surface, is obtained in the reference point of the robot (2). A specific algorithm searches for the best possible match between the two models resulting from the examination and acquired with the optical sensor of the robot (2). An identified transformation then makes it possible to pass from one reference point to another with a known precision. This is the first registration required by the method of the invention.

An optical navigator (10) also movable on wheels completes the operating device, comprising at least one means for the acquisition of optical signals (11) and one screen (12) to display the data from the sensors, at least some of which can be located in the intervention zone. This screen (12) allows for example a virtual tool to be displayed on an intraoperative imaging scan, by means of which the surgeon sees in real time the movement of his tool, providing valuable help in the case of three-dimensional (3D) navigation. According to an important function performed by the three-dimensional optical navigator (10), any movements of the anatomical area undergoing operation, particularly movement due to the patient's respiration in the case of operations on the vertebral column, are monitored in real time by appropriate sensors monitored by the navigator (10), and the moves made by the robotic arm (3) of the robot (2) follow said movements.

The point cloud created by the laser telemeter connected to the arm (3) of the robot (2) referred to above, is formed by a laser beam operating in the infrared range, whose point of contact with the surface moves over said surface of the patient in question and is detected by the infrared cameras of the navigator. The navigator then acquires in real time a point cloud equivalent to that recorded in the same time by the robot. The second registration of the method of the invention is consequently performed on the basis of the same point cloud recorded simultaneously by the robot (2) and by the optical navigator (10). Each recording is however sent to each separate frame of reference. Subsequent computer processing allows the transfer matrix between the two frames of reference to be calculated.

The method of the invention thus in the end allows an immediate and automatic calculation of the second registration on the basis of the same points cloud recorded in the two reference points of the robot (2) on the one hand and of the optical navigator (10) on the other, and which was originally assigned to the calculation of the first registration.

A separate registration between the reference points of the robot (2) and navigator (10) respectively, as exists in the methods of the prior art, is eliminated, which saves a considerable amount of time. Lastly, the automated approach of the solution described guarantees the repeatability of the method, regardless of any expertise of an operator.

One of the additional advantages of this solution is that it also allows the registration between the reference point relating to the patient and the reference point of an optical navigator (10) to be calculated directly and automatically, via computer processing.

No additional step or any additional equipment is required since only processing by the system is involved.

The examples described with the aid of the figures are not exhaustive as regards the invention, which applies to any registration based on the acquisition of surface data of anatomical areas, or reference surfaces, using a laser optical device.

The invention claimed is:

1. An automated registration method to align virtual coordinate systems, the method comprising:
   capturing a first set of registration points from an anatomical surface of a patient using a first registration system;
   capturing, concurrently with the capturing the first set of registration points, a second set of registration points from the anatomical surface using a second registration system, wherein the locations of the second set of registration points on the anatomical surface match the first set of registration points; and
   calculating a transfer matrix based on at least a portion of the first set of registration points and the second set of registration points to align a first coordinate system with a second coordinate system.

2. The method of claim 1, wherein the first registration system includes an optical distance sensor, and wherein the capturing the first set of registration points includes collecting distance measurements within the first coordinate system using the optical distance sensor.

3. The method of claim 2, wherein the optical distance sensor includes a laser telemeter, and wherein the capturing the first set of registration points includes projecting a laser beam onto the anatomical surface.

4. The method of claim 2, wherein the second registration system includes an optical acquisition means, and wherein the capturing the second set of registration points includes capturing optical signals in the form of light points projected onto the anatomical surface.

5. The method of claim 4, wherein the optical distance sensor and the optical acquisition means are tuned to capture the same wavelengths, and wherein capturing the optical signals includes capturing light generated by the optical distance sensor.

6. The method of claim 1, wherein the capturing the first set of registration points includes manipulating a robotic arm within the first coordinate system to capture the first set of registration points using the first registration system coupled to the robotic arm.

7. The method of claim 6, wherein capturing the second set of registration points includes operating an optical navigation system including the second registration system to capture the second set of registration points.

8. The method of claim 7, wherein the calculating the transfer matrix includes registering the robotic arm with the optical navigation system.

9. An automated registration system for concurrently coordinating between two three-dimensional location systems, the system comprising:
- a first three-dimensional location system including an optical distance sensor, the first three-dimensional location system configured to record a first point cloud representing a plurality of locations an anatomical surface of a patient; and
- a second three-dimensional location system including an optical sensor configured to acquire a second point cloud based on capturing light projected onto the anatomical surface by the optical distance sensor during recording the first point cloud;
- a processor configured to calculate a transfer matrix based on at least a portion of the first point cloud and the second point cloud.

10. The automated registration system of claim 9, wherein the optical distance sensor is coupled to a robotic arm operating within a first virtual coordinate system.

11. The automated registration system of claim 10, wherein the second three-dimensional location system is an optical navigation system operating within a second virtual coordinate system.

12. The automated registration system of claim 11, wherein the processor is part of a controller operating the robotic arm, and the processor is configured to use the transfer matrix to transfer location data from the optical navigation system to the robotic arm.

13. The automated registration system of claim 9, wherein the optical distance sensor is a laser telemeter.

14. The automated registration system of claim 13, wherein the optical distance sensor and the optical sensor are tuned to the same wavelengths.

15. The automated registration system of claim 14, wherein the wavelengths are in the infrared range.

16. An automated registration system for concurrently coordinating between two three-dimensional location systems, the system comprising:
- a first three-dimensional location system including a laser telemeter, the first three-dimensional location system configured to record a first point cloud representing a plurality of locations an anatomical surface of a patient; and
- a second three-dimensional location system including an optical sensor configured to acquire a second point cloud based on capturing light projected onto the anatomical surface by the laser telemeter during the recording of the first point cloud;
- a controller including a processor configured to calculate a transfer matrix based on at least a portion of the first point cloud and the second point cloud.

17. The automated registration system of claim 16, further comprising a robotic arm communicatively coupled to the controller and operating within a first virtual coordinate system, wherein the first three-dimensional location system is associated with the robotic arm.

18. The automated registration system of claim 17, wherein the second three-dimensional location system is an optical navigation system maintaining a second virtual coordinate system used to track objects with a surgical field.

19. The automated registration system of claim 18, wherein the controller is further configured to use the transfer matrix to coordinate movements of the robotic arm within the surgical field based on navigation data received from the optical navigation system.

20. The automated registration system of claim 16, wherein the optical sensor includes an infrared camera tuned to receive light within a wavelength range of the laser telemeter.

* * * * *